(12) United States Patent
Tian et al.

(10) Patent No.: US 11,137,390 B2
(45) Date of Patent: Oct. 5, 2021

(54) LIQUID DISTRIBUTION AND DIAGNOSTIC DEVICE AND SYSTEM

(71) Applicant: MONASH UNIVERSITY, Victoria (AU)

(72) Inventors: Junfei Tian, Victoria (AU); Wei Shen, Victoria (AU); Gil Garnier, Victoria (AU); David Bashforth, Liverpool (GB); Heather McLiesh, Victoria (AU)

(73) Assignee: MONASH UNIVERSITY, Victoria (AU)

( * ) Notice: Subject to any disclaimer, the term of this patent is extended or adjusted under 35 U.S.C. 154(b) by 735 days.

(21) Appl. No.: 15/739,427

(22) PCT Filed: Jun. 17, 2016

(86) PCT No.: PCT/AU2016/050516
§ 371 (c)(1),
(2) Date: Dec. 22, 2017

(87) PCT Pub. No.: WO2016/205875
PCT Pub. Date: Dec. 29, 2016

(65) Prior Publication Data
US 2018/0172711 A1 Jun. 21, 2018

(30) Foreign Application Priority Data
Aug. 7, 2015 (AU) ................................ 2015903162

(51) Int. Cl.
*G01N 33/558* (2006.01)
*G01N 33/52* (2006.01)
(Continued)

(52) U.S. Cl.
CPC ....... *G01N 33/525* (2013.01); *G01N 21/8483* (2013.01); *G01N 33/526* (2013.01);
(Continued)

(58) Field of Classification Search
CPC .... G01N 33/525; G01N 33/526; G01N 33/80; G01N 33/558; G01N 21/8483; G01N 33/54386
(Continued)

(56) References Cited

U.S. PATENT DOCUMENTS

| 4,256,693 A * | 3/1981 | Kondo ................. G01N 33/525 422/422 |
| 2009/0298191 A1 | 12/2009 | Whitesides et al. |
| 2013/0084630 A1 | 4/2013 | Rolland et al. |

FOREIGN PATENT DOCUMENTS

| EP | 0526226 A2 | 2/1993 |
| WO | WO 2009/121037 A2 | 10/2009 |

* cited by examiner

*Primary Examiner* — Christopher L Chin
(74) *Attorney, Agent, or Firm* — BakerHostetler

(57) ABSTRACT

A diagnostic device for analysing properties of an analyte in a sample liquid including: a distribution zone having at least two hydrophilic layers placed one on top of the other, wherein one layer is a top layer (12) and the other is a bottom layer (13); and a detection zone located under the distribution zone, the detection zone having a detection layer (14), wherein: the top layer has one or more openings (15) through which the sample liquid is introduced into the device; the bottom layer having one or more openings (16) connecting the distribution zone to the detection zone; the bottom layer also having a means by which the sample liquid is distributed from the top layer's opening to the detection layer through the bottom layer's opening; and a visual indication results on the detection layer when the sample liquid comes into contact with the detection layer.

16 Claims, 4 Drawing Sheets

(51) Int. Cl.
*G01N 21/84* (2006.01)
*G01N 33/543* (2006.01)
*G01N 33/80* (2006.01)
*G01N 21/77* (2006.01)

(52) U.S. Cl.
CPC ..... *G01N 33/54386* (2013.01); *G01N 33/558* (2013.01); *G01N 33/80* (2013.01); *G01N 2021/7766* (2013.01); *G01N 2021/7793* (2013.01); *G01N 2021/7796* (2013.01)

(58) Field of Classification Search
USPC ....... 422/421, 422, 423, 424, 426, 427, 428, 422/429; 435/287.9, 288.7; 436/169, 436/170
See application file for complete search history.

LIQUID DISTRIBUTION AND DIAGNOSTIC DEVICE AND SYSTEM

CROSS-REFERENCE TO RELATED APPLICATIONS

This application is the National Stage of International Patent Application No. PCT/AU2016/050516 filed Jun. 17, 2016, which claims priority from Australian Patent Application No. 2015902487 filed Jun. 26, 2015 and Australian Patent Application No. 2015903162 filed Aug. 7, 2015, the disclosures of each of which are incorporated herein by reference in their entirety.

FIELD OF THE INVENTION

The present invention is directed to a device, system and method for identifying properties of an analyte in a biofluid and the reporting of those results. While the invention will be described with specific reference to its use in determining a person's blood type, it is to be appreciated that other applications of the invention are also envisaged.

BACKGROUND TO THE INVENTION

Many low cost diagnostic devices and systems have a detection zone, containing a biospecific reagent. These devices and systems require a biofluid that is to be analysed to be distributed all over the detection zone. The problem with these devices and systems is that the wettability of an analyte is controlled by the detection zone. If the detection zone is hydrophobic, as fixed by the analytical chemistry of the biospecific reagent, no wetting and/or distribution of liquid throughout the system will occur. Unfortunately, many adsorbed proteins and antibodies render the surface of a detection zone hydrophobic, thus limiting any wetting by most biofluids, and hence limiting the usefulness of the devices.

Some of the difficulties of the prior art will be explained by using blood grouping testing as an example. Blood group testing is carried out by mixing blood grouping antibodies with the patient's blood sample. A blood grouping antibody binds specifically with the corresponding antigens on the surface of red blood cells, leading to a haemagglutination reaction through which the agglutinated red blood cells will precipitate out from the plasma phase. However, if an antibody is mixed with a blood sample where the corresponding antigen is absent from the surface of the red blood cells, the haemagglutination reaction will not occur and no precipitation of the red blood cells will occur. By visually observing the presence (or absence) of the agglutinated lumps of red blood cells from the sample-antibody mixture the blood grouping of a blood sample is determined.

Existing blood grouping devices or kits are operated by adding blood grouping antibodies with a patient's blood sample and observing the separation of blood red cells from the blood plasma. The blood grouping result is then identified through observing the agglutination of red blood cells visually or by some instruments. A drawback of this approach is that the tests need to be done through handing of antibody solutions, or instruments. Interpretation of test results must be carried out by trained medical nurses or other trained people who have the knowledge to understand the results.

It is an object of the present invention to overcome or ameliorate problems and difficulties of the prior art.

Discussion or mention of any piece of prior art in this specification is not to be taken as an admission that the prior art is part of the common general knowledge of the skilled addressee of the specification in Australia or any other country.

SUMMARY OF THE INVENTION

According to a first aspect of the present invention, there is provided a diagnostic device for analysing properties of an analyte in a sample liquid including: a distribution zone having at least two hydrophilic layers placed one on top of the other, wherein one layer is a top layer and the other is a bottom layer; and a detection zone located under the distribution zone, the detection zone having a detection layer, wherein: the top layer has one or more openings through which the sample liquid is introduced into the device; the bottom layer having one or more openings connecting the distribution zone to the detection zone; the bottom layer also having a means by which the sample liquid is distributed from the top layer's opening to the detection layer through the bottom layer's opening; and a visual indication results on the detection layer when the sample liquid comes into contact with the detection layer.

The device preferably includes a gap between the hydrophilic layers which separates the hydrophilic layers. Alternatively, or in addition, the device may include a gap between the distribution zone and the detection zone. The gap is preferably between 1 nm to 1 cm in height, and more preferably between 1 nm to 1 mm in height.

The gap separating the hydrophilic layers may be formed by adhesive which also connects the hydrophilic layers together. Alternatively, or in addition, the gap between the distribution zone and the detection zone may be formed by an adhesive which also connects the zones together.

Preferably each hydrophilic layer is a film. More preferably the film is made of flexible material. The hydrophilic layers may be made of paper, non-woven material, metal, inorganic material or polymer, including Polyolefin (PE, PP), polyesters (PET, PLA), cellulosics, polyurethanes, PS, PC and their copolymers and blends.

The hydrophilic layers may be surface treated or alternatively not surface treated to enhance water/liquid wettability, including plasma treatment, radiation treatment, surface coating, adsorption of surfactant or polymer, or adsorption of biomolecules.

The at least two hydrophilic layers may be made of the same material, or alternatively, they can be made of different materials.

No matter the material, it is preferable that the hydrophilic layers are made of material in which the contact angle formed by a droplet of liquid to be analysed is less than 90 degrees.

Preferably the hydrophilic layers are clear or translucent.

It is preferable that the visual indication occurs from symbols or text providing details of the properties of the sample liquid analyte.

The detection zone may include a hydrophilic semi-permeable layer that can perform filtration or elution for sample preparation prior to being detected on the detection layer.

The device preferably also includes a reporting zone. The detection and reporting zones may be integral with each other, or one and the same, or they may be separate.

The device may also include an absorption zone located below the detection zone.

The device preferably also includes a casing or protective layer surrounding the device.

The detection zone may contain a binding element, and if so, the binding agent preferably includes antibodies and/or antigen.

The means by which the sample liquid is distributed from the device's top layer's opening to the detection layer is preferably via a pattern including grooves, holes, and/or stripes in or on the hydrophilic bottom layer.

The detection layer or a surface of the detection layer is preferably made of paper, cellulosic or non-woven material.

The device is preferably used for blood analysis or blood typing.

According to a further aspect of the invention, there is provided a method of using a diagnostic device according to any one of the preceding claims, including:

a) introducing the sample fluid through the one or more openings of the top layer, and subsequently b) viewing the visual indication results on the detection layer.

An eluent may optionally be introduced through the one or more openings of the top layer.

According to another aspect of the present invention there is provided a diagnostic system incorporating a diagnostic device as described above.

According to a further aspect of the present invention, there is provided a diagnostic test kit incorporating a diagnostic device as described above.

BRIEF DESCRIPTION OF THE DRAWINGS

It will be convenient to further describe the invention with respect to the accompanying drawings. Other embodiments of the invention are possible, and consequently, the particularity of the accompanying drawings is not to be understood as superseding the generality of the preceding description of the invention. In the drawings.

DESCRIPTION OF PREFERRED EMBODIMENT

The device of the present invention identifies properties of an analyte in a biofluid and reports those results. It provides a simple, inexpensive and one-step biofluid distribution device and result reporting system. The device distributes any biofluid that is to be analysed over the detection area in a single step. The device does not require external power to distribute the biofluid or to obtain results, nor does the device use a diluent or carrier liquid to assist the distribution of the biofluid or to obtain results.

Figure 1:
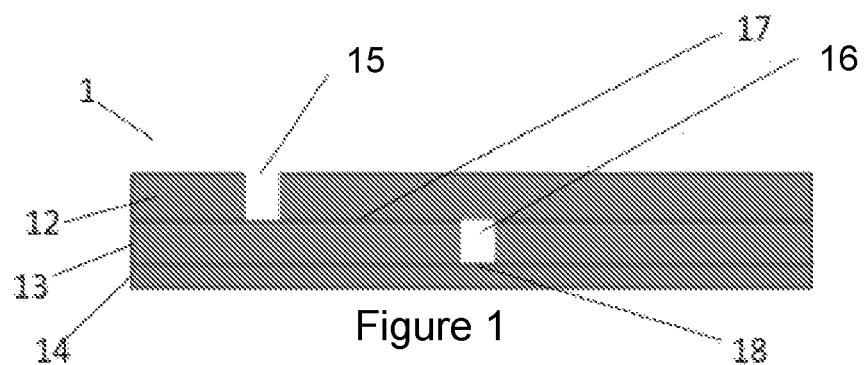
FIG. 1 shows a cross-sectional schematic of a biofluid diagnostic device according to a first embodiment of the present invention.
Figure 2:
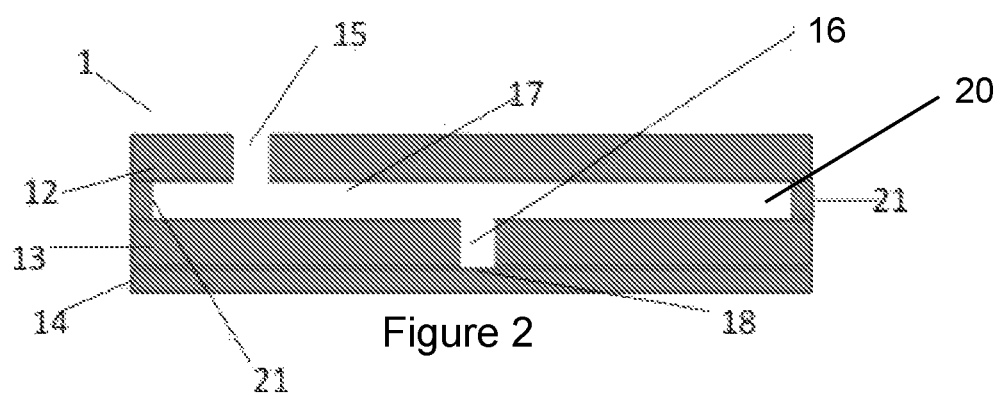
FIG. 2 shows a cross-sectional schematic of a biofluid diagnostic device according to a second embodiment of the present invention.
Figure 3:
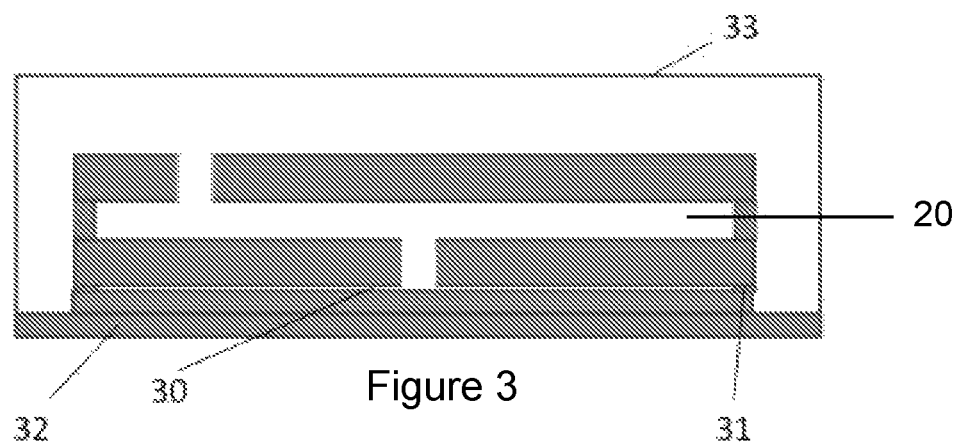
FIG. 3 shows a cross-sectional schematic of a biofluid diagnostic device according to a third embodiment of the present invention.

FIGS. 1, 2 and 3 each show a cross-section of a biofluid diagnostic device 1 according to different embodiments of the present invention. The device includes a biofluid distribution device having at least two hydrophilic layers. In FIGS. 1, 2 and 3 a top hydrophilic layer 12 and a bottom hydrophilic layer 13 are sandwiched together. These two layers form the biofluid distribution zone of the device. Although the layers 12, 13 are sandwiched together, in one embodiment they are separated by a small gap 20 as shown in FIGS. 2 and 3. The gap 20 between the layers 12, 13 can be between approximately 1 nm to 1 cm in height, but preferably between 1 nm to 1 mm in height. As shown in FIGS. 2 and 3, the top 12 and bottom 13 layers may be joined or connected together by some form of adhesive 21, which bonds the layers together and/or serves to create the gap 20 between the top layer 12 and bottom layer 13. Alternatively, the top layer 12 may simply be placed on top of the bottom layer 13, as shown in FIG. 1, and the natural gap left when the two layers are connected can, in certain applications, be sufficient for biofluid to flow between the layers.

In embodiments of a biofluid diagnostic device, a detection zone is located below the fluid distribution zone. The detection zone includes a detection layer 14 which is located under the bottom layer 13 of the biofluid distribution device. The detection layer 14 identifies the properties of the analyte in the biofluid that is being tested and reports those results. The detection layer 14 may be in direct contact with the bottom layer 13 of the biofluid distribution zone as shown in FIGS. 1 and 2. Alternatively, there may be a small gap 30 between the bottom distribution layer 13 and the detection layer 14. Again, the distribution layer 13 and detection layer 14 may be joined or connected together by some form of adhesive 31, which bonds the layers together and/or serves to create the gap 30 between the bottom layer 13 and the top of the detection layer 14.

In addition, the detection zone may further include a reporting layer (not shown). The reporting layer may be separate from the detection layer. Alternatively, the reporting layer may be integral with the detection layer.

An absorbent layer 32, as shown in FIG. 3 can be placed underneath the detection layer/zone 14. As shown in FIG. 3, the biofluid distribution zone and detection zone can be encased in a protective layer or holder 33.

As shown in FIGS. 1, 2 and 3, the top layer 12 has a hole 15 or port through which the biofluid sample to be analysed is dispensed into the device. If required, any washing solutions (eluent) can also be introduced through this hole 15. The bottom layer 13 may contain grooves, holes or any patterns through which the fluid can flow through using capillary action to reach an opening 16 in the bottom layer 13 which allows the fluid access to the detection zone and layer 14.

This arrangement creates a wettable channel 17 through which the biofluid which is to be analysed first flows in the x-y dimensions by capillary action all over the distribution zone formed by the top and bottom layers, before it is distributed onto the detection zone 18 (in the z direction) thought the slips/holes 16 of the bottom layer 13.

Figure 6:
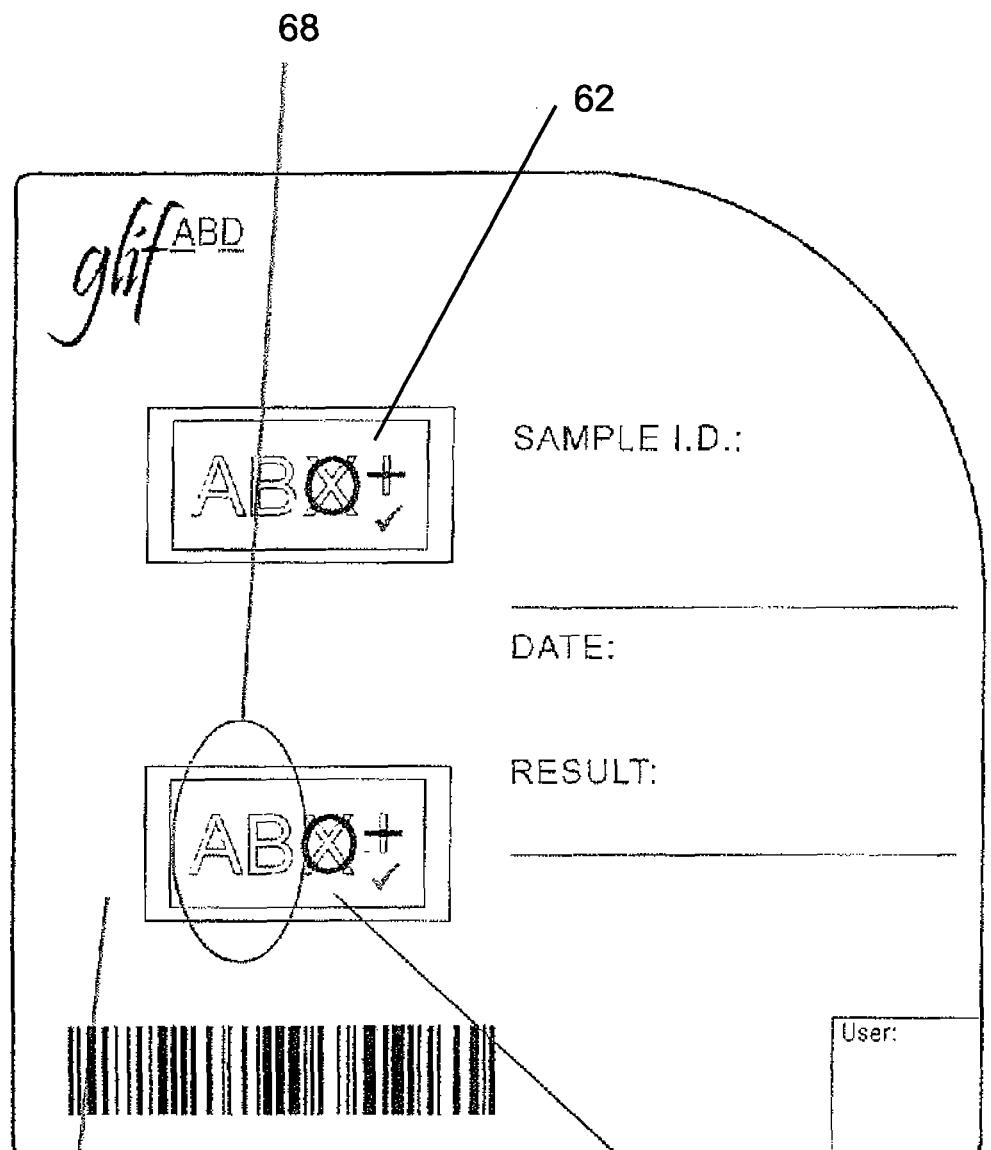
FIG. 6 shows a biofluid diagnostic device of the present invention.

The hydrophilic layers forming the biofluid distribution zone are preferably films made of wettable plastic material. Typically these plastic films are transparent. This enables the result of the analysed biofluid, which is visually observed on the detection zone or can be measured by the detection zone, to be seen through the transparent layers. The visual indication can be achieved by printing text or symbols on to the detection layer with a binding or molecules which react with the biofluid sample that is being analysed. An example of this is shown in FIG. 6. A biofluid diagnostic device 61 is incorporated into a test kit 69. In this embodiment, the test kit contains a second diagnostic device 62. A blood sample from a patient is provided to the first diagnostic device which provides a visual indication of the result of the blood typing test, for example, A, B or O as well as − and +. It is envisaged that other symbols may also be used. To verify the result of the blood test a second blood sample from the patient is provided to the second diagnostic device 62 which also provides a visual indication of the result of the blood typing test. The results from the two diagnostic devices should be the same. In FIG. 6, it is clear that the blood contained in the bag is A+ (A positive blood) as shown by the symbol 68. Details of the sample taken, date and blood type result can also be written on the test kit as shown in FIG. 6. Such a test kit is extremely advantageous especially for developing countries or remote areas where medical clinics and hospitals are not as structured. This test kit with diagnostic devices incorporated within it will enable patients to hold on to a record which states their blood type while they wait for other medical treatment. Unlike conventional records where a patient's blood type is simply written down, errors cannot occur in this test kit and record of blood type. This is because the blood sample is used to provide the visual indication which states the blood type. Further, the diagnostic devices 61 and 62, draw the blood away from the surface of the device and test kit so that a patient or other person will not come in contact with the blood sample.

In another embodiment (not shown) a biofluid diagnostic device is incorporated into a blood bag. In this embodiment, the blood does not need to be tested before it is put in the bag. By having the biofluid diagnostic device incorporated into the bag, the biofluid diagnostic device provides a visual indication 68 as to the blood type that is contained in the bag without the need for duplicate testing or to withdraw fluid from the bag. This provides for a more sanitary product and ensures that the blood is not contaminated in any way.

The detection layer is preferably paper or cellulosic material. However, the detection layer may have a biosensor printed or impregnated into it. Alternatively, the detection layer may be a sensing medium made of paper, plastic, metal and/or glass which when brought into contact with the biofluid test sample detects or transmits a result of the analysed biofluid (test sample) directly by visual interpretation. Alternatively, it may detect or transmit the result indirectly via photoelectric amplification or image analysis.

Figure 4:
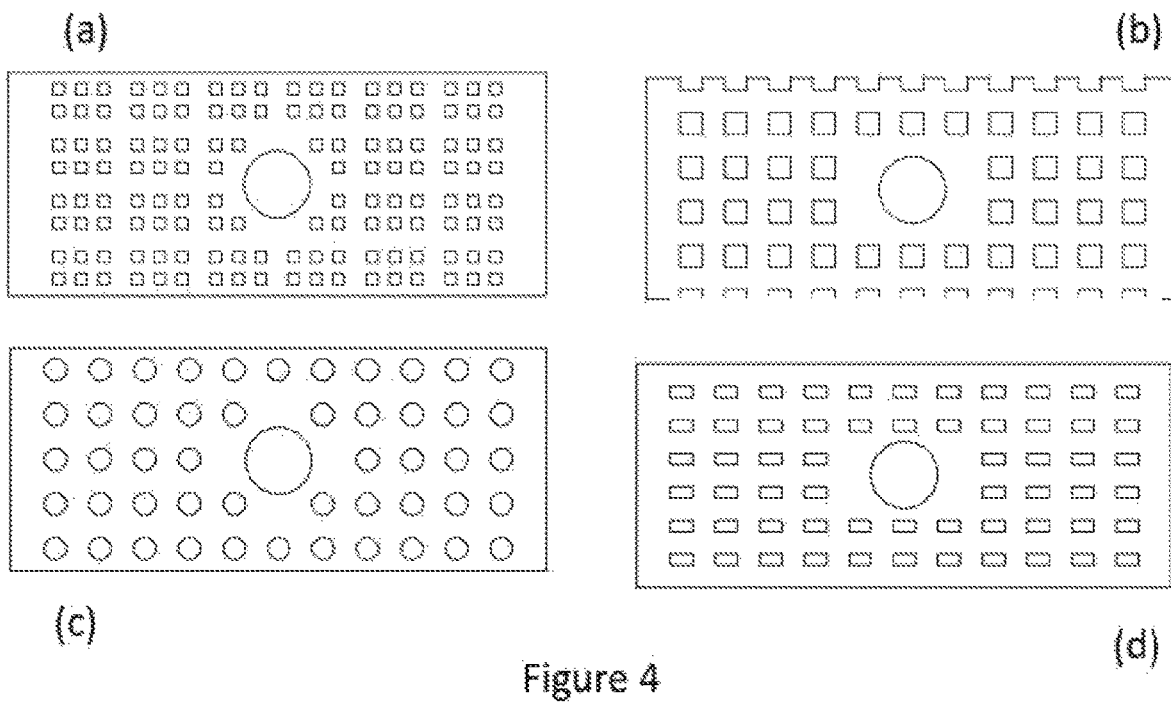
FIGS. 4(a), (b), (c) and (d) show various embodiments of a hydrophilic layer of the biofluid diagnostic device.
Figure 5:
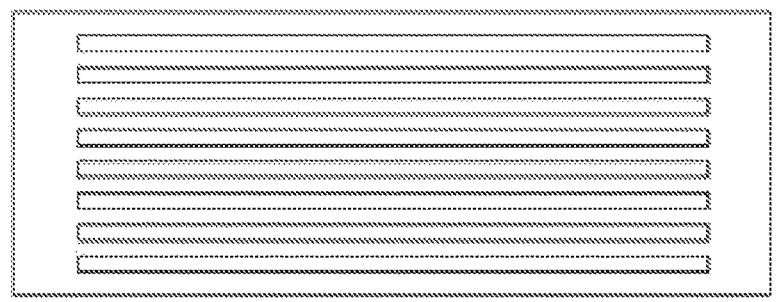
FIG. 5 shows an embodiment of another hydrophilic layer of the biofluid diagnostic device.

The present invention in one embodiment can be used as a sample distribution and diagnostic device in a blood typing sensor. In this embodiment (not shown), the sample distribution device rapidly and evenly distributes the blood sample onto the detection zone which is a bioactive paper component. The bioactive paper component carries an antibody text pattern. The sample distribution device uses a capillary wicking driving force to deliver a biofluid sample to the entire analytical area of the bioactive paper component. In this embodiment, the device consists of two polymer film layers on which different cutting patterns have been fabricated. Examples of polymer films with different cutting patterns are shown in FIGS. 4 and 5. On the first layer of polymer film rectangular holes were cut in parallel to allow liquid penetration along the holes. An example of such an embodiment is shown in FIG. 4(d). On the second layer of polymer film, a series of parallel rectangular slots are cut; an example of such an embodiment is shown in FIG. 5. The liquid distribution device is then formed by overlapping the two layers of polymer films. The biofluid sample wicks through all gaps between the two films and is delivered to the detection zone and onto the paper surface of the detection layer where a visual indication occurs providing a result of the biofluid sample.

Figure 7:
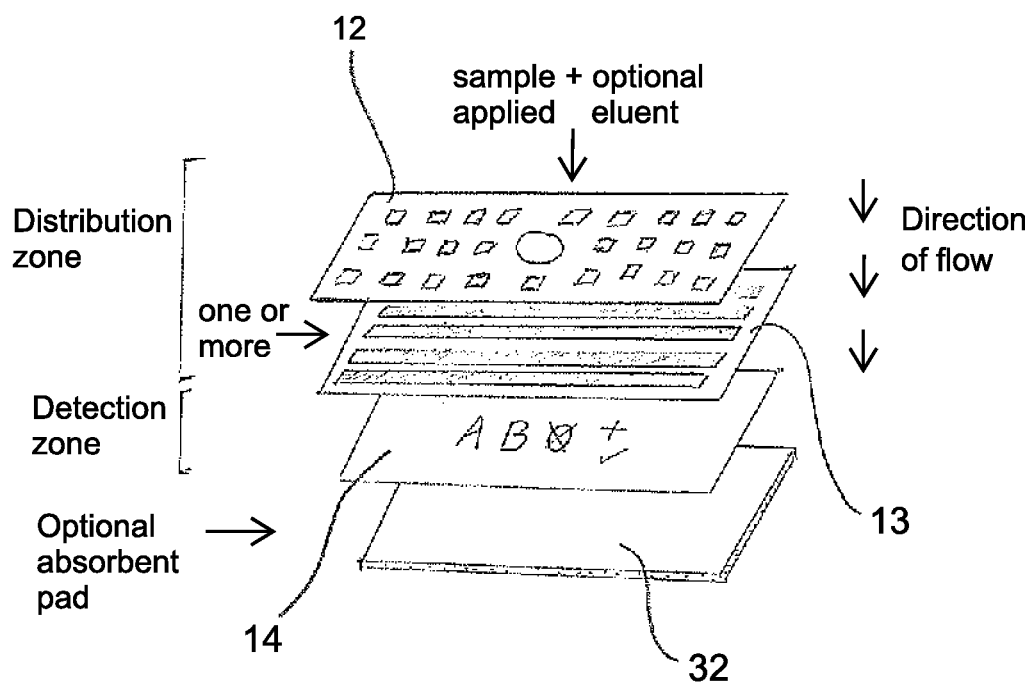
FIG. 7 shows an exploded perspective view of the biofluid diagnostic device of the present invention.

FIG. 7 shows an exploded view of the diagnostic device. The top and bottom hydrophilic layers 12, 13 together form the distribution zone of the device. The underlying detection layer 14 forms the detection zone of the device. An optional absorbent pad 32 can be placed under the detection layer 14.

As explained, the sample distribution system contains one or more than one layer of patterned films or sheets manufactured to incorporate in liquid management structures. In the embodiment shown in FIG. 6 two layers of patterned polymer films were used to build the liquid distribution system. The top and bottom layers were made with polymer films that have different liquid management structures. These layers were stuck together by appropriate adhesives. It was then placed in such a way that the liquid distribution system was in contact with the bioactive substrate. The sample is introduced to the device through the top polymer film. In the example shown in FIG. 4 it can be seen that the sample is introduced from the middle hole, but it can be designed in different ways. The sample can be distributed to the entire bioactive substrate.

A second liquid can be introduced on the top polymer film and can flow through to the bioactive substrate to either react or clean the first liquid (that is, the sample to be tested).

This biofluid sample distribution device distributes liquid uniformly on a material surface, irrespective whether the material is wettable or not. This biofluid sample distribution device will allow a new generation of paper-based microfluidics to be made. Paper sensors made with a liquid distribution device will allow liquid to be distributed on paper, irrespective whether the paper is hydrophobic or not.

With this design principle, many other arrangements based on the present invention sample distribution and diagnostic device and system are possible. Other embodiments may include using more than one layer of polymer film with different cutting patterns, for example as shown in FIGS. 4(a), (b), (c) and (d). One or more than one layer of polymer film with cut or embossed 'V' or 'U' shaped grooves or holes of different shapes may be used. Alternatively, one or more than one layer of polymer film could be used to form folded structures by origami with different cutting patterns.

The present invention will advantageously lead to an entirely different design of paper-based microfluidic sensors because the paper component no longer needs to be hydrophobic to work.

A key advantage of the present invention is that the liquid distribution process is independent of the wettability of the detection zone. This is an important feature of the invention because the device manufacturing process and detection chemistry can be optimized independently from the ability of the fluid to wet and be distributed over the detection zone.

The biofluid distribution system and biofluid diagnostic device and system may also be used for immediate spreading of all aqueous media. It may be used for any analysis purpose including but not limited to in vitro diagnostic devices (IVDs), microscopic examination of bacteria, animal or plant aqueous cellular suspensions directly or after modification by media which can either be added to or incorporated in the manufacture of the device. Other applications for the device include examination of inanimate particles by light or electron microscopy or any application requiring a substrate as described for the present invention.

The examples explained above focus on identifying blood type or blood group. However this testing device could also be used to identify properties of other biofluids including plasma, serum, urine, amitotic fluid, semen, saliva, sweat, tears, cerebrospinal fluid, sinovial fluid or effusion. It could also be used to ascertain if a blood sample is infected with HIV or other illnesses. The biofluid can be collected by any conventional means including but not limited to venepuncture, stab, excretion, secretion or aspiration.

As the present invention may be embodied in several forms without departing from the essential characteristics of the invention, it should be understood that the above described embodiment should not be considered to limit the present invention but rather should be construed broadly. Various modifications and equivalent arrangements are intended to be included within the spirit and scope of the invention. Modifications and variations as would be deemed obvious to the person skilled in the art are included within the ambit of the present invention as claimed in the appended claims.

The claims defining the invention are as follows:

1. A diagnostic device for analysing properties of an analyte in a biofluid sample including:
    a distribution zone having at least two hydrophilic layers placed one on top of the other, with a gap therebetween wherein one layer is a top layer and the other is a bottom layer; and
    a detection zone located under the distribution zone, the detection zone having a detection layer with a binding element for identifying the properties of the analyte in the biofluid,
    wherein:
        the top layer has one or more openings through which the biofluid sample is introduced into the device, and a pattern containing at least one of: grooves, holes and stripes by which the biofluid sample introduced via the top layer's opening is distributed by capillary action to reach the bottom layer;
        the bottom layer also has a pattern containing at least one of: grooves, holes, and stripes by which the biofluid sample distributed from the top layer is distributed by capillary action to reach the detection layer; and
        the detection layer has text or symbols thereon providing a visual indication of the properties of the analyte in the biofluid sample when the biofluid sample comes into contact with the binding element.

2. A diagnostic device according to claim 1, wherein the gap between the hydrophilic layers is between 1 nm to 1 mm in height.

3. A diagnostic device according to claim 2, wherein the hydrophilic layers are separated by a gap which is formed by adhesive connecting the hydrophilic layers together.

4. A diagnostic device according to claim 1, further including a gap between the distribution zone and the detection zone, the gap being between between 1 nm to 1 mm in height.

5. A diagnostic device according to claim 4, wherein the gap between the distribution zone and the detection zone is formed by an adhesive connecting the zones together.

6. A diagnostic device according to claim 1 wherein each hydrophilic layer is a film.

7. A diagnostic device according to claim 1 wherein the hydrophilic layers are made of paper, non-woven material, metal, inorganic material or polymer.

8. A diagnostic device according to claim 1, wherein the hydrophilic layers are surface treated or not surface treated to enhance water/liquid wettability, including plasma treatment, radiation treatment, surface coating, adsorption of surfactant or polymer, or adsorption of biomolecules.

9. A diagnostic device according to claim 8 wherein the hydrophilic layers are made of material in which the contact angle formed by a droplet of biofluid sample to be analysed is less than 90 degrees.

10. A diagnostic device according to claim 1, wherein the hydrophilic layers are clear or translucent.

11. A diagnostic device according to claim 1, wherein the detection zone includes a hydrophilic semi-permeable layer that can perform filtration or elution for sample preparation prior to being detected on the detection layer.

12. A diagnostic device according to claim 1, wherein the binding element includes antibodies and antigen.

13. A diagnostic device according to claim 1, wherein the detection layer or a surface of the detection layer is made of paper, cellulosic or non-woven material.

14. A diagnostic device according to claim 1, wherein the device is to be used for blood analysis or blood typing.

15. A diagnostic device according to claim 1, wherein the hydrophilic layers are made of polyolefin, polyester, cellulosics, polyurethane, polystyrene, polycarbonate and their copolymers and blends.

16. A diagnostic device according to claim 1 wherein the hydrophilic layers are made of polyethylene, polypropylene, polyethylene terephthalate, polylactide and their copolymers and blends.

* * * * *